US00RE46105E

(19) United States
(12) Reissued Patent
Yonehara

(10) Patent Number: US RE46,105 E
(45) Date of Reissued Patent: *Aug. 16, 2016

(54) METHOD OF SELECTIVELY DETERMINING GLYCATED HEMOGLOBIN

(71) Applicant: ARKRAY, Inc., Kyoto (JP)

(72) Inventor: Satoshi Yonehara, Kyoto (JP)

(73) Assignee: ARKRAY, Inc., Kyoto (JP)

( * ) Notice: This patent is subject to a terminal disclaimer.

(21) Appl. No.: 14/521,534

(22) Filed: Oct. 23, 2014

Related U.S. Patent Documents

Reissue of:
(64) Patent No.: 7,235,378
Issued: Jun. 26, 2007
Appl. No.: 10/332,790
PCT Filed: Jul. 12, 2001
PCT No.: PCT/JP01/06064
§ 371 (c)(1),
(2) Date: Apr. 14, 2003
PCT Pub. No.: WO02/06519
PCT Pub. Date: Jan. 24, 2002

U.S. Applications:
(63) Continuation of application No. 14/329,019, filed on Jul. 11, 2014, which is an application for the reissue of Pat. No. 7,235,378.

(30) Foreign Application Priority Data

Jul. 14, 2000 (JP) ..... 2000-214801

(51) Int. Cl.
*C12Q 1/54* (2006.01)
*C12Q 1/26* (2006.01)
*G01N 33/72* (2006.01)
*C12Q 1/37* (2006.01)

(52) U.S. Cl.
CPC .. *C12Q 1/26* (2013.01); *C12Q 1/37* (2013.01); *G01N 33/723* (2013.01); *G01N 33/725* (2013.01)

(58) Field of Classification Search
CPC ..... C12Q 1/005; C12Q 1/26; C12Q 1/37
See application file for complete search history.

(56) References Cited

U.S. PATENT DOCUMENTS

| | | | | | |
|---|---|---|---|---|---|
| 3,914,436 | A | * | 10/1975 | Nakadai et al. | 426/46 |
| 5,370,990 | A | * | 12/1994 | Staniford et al. | 435/4 |
| 5,387,109 | A | * | 2/1995 | Ishikawa et al. | 435/191 |
| 5,631,140 | A | * | 5/1997 | Kobold et al. | 435/23 |
| 5,712,138 | A | * | 1/1998 | Kato et al. | 435/189 |
| 6,033,867 | A | * | 3/2000 | Kato et al. | 435/25 |
| 6,352,835 | B1 | * | 3/2002 | Komori et al. | 435/25 |
| 6,790,665 | B2 | * | 9/2004 | Yonehara et al. | 436/66 |
| 6,825,016 | B1 | * | 11/2004 | Ishimaru et al. | 435/183 |
| 7,070,948 | B1 | * | 7/2006 | Sakaue et al. | 435/23 |
| 2002/0025546 | A1 | * | 2/2002 | Komori et al. | 435/28 |
| 2004/0247587 | A1 | * | 12/2004 | Ishimaru et al. | 424/94.63 |

FOREIGN PATENT DOCUMENTS

| | | | | |
|---|---|---|---|---|
| CN | 1280241 | A | | 1/2001 |
| EP | 0 072 440 | A1 | * | 2/1983 |
| EP | 0526150 | A1 | | 2/1993 |
| EP | 0576838 | A2 | | 1/1994 |
| EP | 0598329 | A2 | | 5/1994 |
| EP | 0678576 | A2 | | 10/1995 |
| EP | 0693559 | A1 | | 1/1996 |
| EP | 0864647 | A1 | | 9/1998 |
| EP | 0919632 | A2 | | 6/1999 |
| EP | 0921198 | A1 | | 6/1999 |
| EP | 1 002 874 | | | 5/2000 |
| EP | 1002874 | A2 | | 5/2000 |
| EP | 1 223 224 | | | 7/2002 |
| EP | 1223224 | A1 | | 7/2002 |
| JP | H02-88568 | A | | 3/1990 |
| JP | 2-195900 | | * | 8/1990 |
| JP | 02-195900 | A | | 8/1990 |
| JP | H08-208492 | A | | 8/1996 |
| JP | 2000-300294 | | | 10/2000 |
| JP | 2000-300294 | A | | 10/2000 |
| JP | 2001-54398 | | | 2/2001 |
| JP | 2001-54398 | A | | 2/2001 |
| JP | 2001-95598 | A | | 4/2001 |
| JP | 2001-204495 | | | 7/2001 |

(Continued)

OTHER PUBLICATIONS

Ajabnoor et al. "*Bacillus subtilis* aminopeptidase: Specificity toward amino acid amides, dipeptides and oligopeptides" Arch Biochem Biophys 202(2) 540-545 (1980).*
Yoshida et al., "Primary structures of fungal fructosyl amino acid oxidases and their application to the measurement of glycated proteins" Eur. J. Biochem. 242, 499-505 (1996).*
Rice et al. "The papain digestion of native, denatured and 'stabilized' human serum albumin" J. Biol Chem. 158:609-617 (1945).*
Iberg et al. "Nonenzymatic Glycosylation of Albumin in Vivo Identification of Multiple Glycosylated Sites" J. Biol Chem. 261:13542-13545 (1986).*
BIOZYM http://www.biozym.de/datasheets/bromelain.php [accessed Apr. 13, 2015].*

(Continued)

*Primary Examiner* — Bruce Campell
(74) *Attorney, Agent, or Firm* — Morgan, Lewis & Bockius LLP

(57) ABSTRACT

A method of determining glycated hemoglobin is provided, by which a ratio of the glycated hemoglobin in a sample can be determined accurately and easily. The ratio of glycated hemoglobin can be determined by degrading a glycated hemoglobin in a whole blood sample selectively with a protease to give a glycated hemoglobin degradation product; causing a redox reaction between a glycation site of the glycated hemoglobin degradation product and a fructosyl amino acid oxidoreductase; and determining this redox reaction. Further, as shown in FIG. 1, in a whole blood sample, there is a correlation between the ratio of the glycated hemoglobin determined by this method and an HbA1c concentration. Thus, without determining the glycated α-amino group as a characteristic structure of HbA1c, an amount of HbA1c can be determined accurately and easily from the determined ratio of the glycated hemoglobin.

16 Claims, 2 Drawing Sheets

(56) References Cited

FOREIGN PATENT DOCUMENTS

| | | | | |
|---|---|---|---|---|
| JP | 2001-204495 | A | | 7/2001 |
| WO | 97/13872 | A1 | | 4/1997 |
| WO | WO 97/13872 | | * | 4/1997 |
| WO | 98/48043 | A1 | | 10/1998 |
| WO | WO 98/48043 | | * | 10/1998 |
| WO | 01/25475 | | | 4/2001 |
| WO | 01/25475 | A1 | | 4/2001 |

OTHER PUBLICATIONS

Shapiro et al. "Sites of Nonenzymatic Glycosylation of Human Hemoglobin A" J Biol Chem 255(7): 3120-3127 (1980).*
Termination of opposition proceedings of European Patent No. 1304385 dated Jan. 18, 2013.
Letter declaration withdrawal of opposition in European Patent No. 1304385 dated Nov. 17, 2011.
Filing of Opposition Proceedings in European Patent No. 1304385 dated Sep. 28, 2011.
Patentee's Reply to Notice of Opposition Proceedings in European Patent No. 1304385 dated May 18, 2012.
European Search Report issued in European Patent Application No. 10010191 dated Aug. 2, 2011.
Experimental Data Certificate submitted in corresponding European Patent Application No. 01947995.5 dated Jun. 16, 2008.
Submission of publications to Commissioner of Patents in Japanese Patent Application No. 2007-038171 dated Jun. 4, 2008 (translation only).
Submission of publications to Commissioner of Patents in Japanese Patent Application No. 2007-038171 dated Jul. 31, 2008 (translation only).
Submission of publications to Commissioner of Patents in Japanese Patent Application No. 2007-038171 dated Jan. 16, 2009 (translation only).
International Preliminary Examination Report issued in PCT/JP01/06064 dated Apr. 12, 2002.
European Search Opinion issued in European Patent Application No. 10010191.4 dated Apr. 2, 2014.
Sakurabayashi et al., "New Enzymatic Assay for Glycohemoglobin," Clinical Chemistry, American Association for Clinical Chemistry, 49: 269-274 (2003).
European Search Report issued in related European Patent Application No. 01947995 dated Mar. 26, 2006.
Japanese Office Action issued in related Japanese Patent Application No. 2002-512410 mailed May 29, 2006.
Gil et al., "Effect of non-enzymaqatic glycosylation on reactivity in proteolysis," Acta Cient Venez, 42: 16-23 (1997).
Office Action issued in related Japanese Patent Application No. 2002-512410 dated Jan. 9, 2007.
International Search Report issued in related PCT/JP2001/06064 dated Sep. 18, 2001.
Extended European Search Report issued in corresponding European Patent Application No. 15174619.5 dated Sep. 24, 2015.
Gil H, Mata-Segreda J, Schowen R. Acta Cient. Venez. (1997) 42, 16-23 Effect of non-enzymaqatic glycosylation on reactivity in proteolysis. Article in Spanish.*
EPO Search Report for PCT/JP01/06064 Provided by Applicant. Sakurabayashi, et al., "New Enzymatic Assay for Glycohemoglobin", Clinical Chemistry, American Association for Clinical Chemistry, Washington. DC 49:2, 269-274 (2003).

* cited by examiner

METHOD OF SELECTIVELY DETERMINING GLYCATED HEMOGLOBIN

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 7,235,378. The reissue applications are application Ser. No. 14/329,019 filed Jul. 11, 2014; Ser. No. 14/521,525 filed Oct. 23, 2014; Ser. No. 14/521,528 filed Oct. 23, 2014; and Ser. No. 14/521,534 (the present application) filed Oct. 23, 2014, the last three of which are continuation reissues of application Ser. No. 14/329,019.*

TECHNICAL FIELD

The present invention relates to a method of determining an amount of glycated hemoglobin present in whole blood.

BACKGROUND ART

Glycated hemoglobin in blood has served as an important index for the diagnosis, treatment, etc. of diabetes because it reflects previous blood glucose levels in vivo.

The determination of such glycated hemoglobin has been carried out, for example, by high performance liquid chromatography (HPLC), a minicolumn method, immunoassays, and the like. According to these methods, the amount or ratio of hemoglobin that has been glycated can be determined. Recently, an enzymic method that enables the determination of glycated proteins by means of a fructosyl amino acid oxidoreductase (FAOD) has been developed, and attempts have been made to determine an amount of hemoglobin that has been glycated (i.e., glycated hemoglobin) by this enzymic method.

DISCLOSURE OF INVENTION

However, the above-mentioned method has a problem as follows. Because the glycated hemoglobin is a component contained in a blood cell, it is absolutely necessary to hemolyze the blood cell to carry out the determination of the glycated hemoglobin. In the case where a sample to be analyzed is whole blood, however, the treatment for causing hemolysis (hereinafter, referred to as "hemolysis treatment") conducted on the whole blood brings about a state where blood cell components and plasma components are mixed with each other. Thus, the whole blood sample that has been subjected to the hemolysis treatment contains not only the glycated hemoglobin as a blood cell component but also albumin as a high-content plasma component and glycated albumin as a glycation product thereof, in particular. The glycated albumin is determined together with the glycated hemoglobin because FAOD also acts on the glycated albumin. On this account, a complicated process for separating the plasma and blood cells from the whole blood sample is required in order to eliminate the effect of other glycoproteins such as the glycated albumin and the like.

Therefore, it is an object of the present invention to provide a method of determining an amount of glycated hemoglobin, which allows the effect of other glycoproteins to be eliminated without separating plasma and blood cells in a whole blood sample so that an amount of glycated hemoglobin in the whole blood sample is determined accurately and easily.

In order to achieve the above object, a method of determining an amount of glycated hemoglobin according to the present invention includes: degrading glycated hemoglobin in whole blood selectively with a protease to give a glycated hemoglobin degradation product; causing a redox reaction between a glycation site of the glycated hemoglobin degradation product and FAOD; and determining the redox reaction to determine an amount of the glycated hemoglobin. The term "an amount of glycated hemoglobin" as used in the present invention also includes a ratio of glycated hemoglobin.

If the glycated hemoglobin is distinguished from other proteins and peptides and is degraded selectively (i.e., specifically) with a protease as described above, it becomes possible to determine an amount of the glycated hemoglobin while eliminating the effect of other glycoproteins, especially glycated albumin, without separating blood cells from the whole blood because FAOD hardly acts on proteins or long polypeptide chains. Thus, a sample to be used in this method may be whole blood that has been subjected to a hemolysis treatment, for example.

In the method of the present invention, in order to degrade glycated hemoglobin selectively, a protease capable of degrading the glycated hemoglobin selectively, for example, may be used as the protease. Further, in the present invention, a method of degrading glycated hemoglobin selectively is not limited to the use of the protease capable of degrading the glycated hemoglobin selectively. The glycated hemoglobin may be degraded selectively by any other means. Also, the protease capable of degrading glycated hemoglobin selectively may be used in combination with one or more of ordinary proteases.

It is preferable that the protease capable of degrading glycated hemoglobin selectively is at least one of bromelains, papains, trypsins derived from porcine pancreas, metalloproteinases, and proteases derived from Bacillus subtilis. Examples of the proteases derived from Bacillus subtilis include Protease N (trade name, available from Sigma Aldrich Co.), Protease N "AMANO" (trade name, available from Amano Enzyme Inc.), and the like. Examples of the metalloproteinases include a metalloproteinase derived from the genus Bacillus (EC 3. 4. 24. 4) (e.g., available from Toyobo Co., Ltd. under the trade name Toyoteam), and the like. Among these, the metalloproteinases, bromelains, and papains are more preferable, and the metalloproteinases are most preferable.

In the method of the present invention, it is preferable that a substrate of the FAOD is at least one glycated amine selected from the group consisting of glycated proteins, glycated peptides, and glycated amino acids, and the FAOD acts on at least one of a glycated α-amino group and a glyeated side-chain amino group of the glycated amine to catalyze a reaction that causes generation of hydrogen peroxide.

In the method of the present invention, the glycation site of the glycated hemoglobin degradation product to be reacted with the FAOD preferably is a glycated amino group in a side chain of an amino acid residue and a glycated α-amino group, for example, whereas the glycation site to be reacted with the FAOD varies depending on the catalytic reaction caused by the FAOD to be used. Preferably, the glycation site is the glycated amino group in a side chain of an amino acid residue because FAOD having a catalytic function as described later can act thereon more easily. Examples of the glycated amino group include a glycated amino group in a side chain of a lysine residue, a glycated amino group in a side chain of an arginine residue, and the like.

In the method of the present invention, it is preferable that the protease is added to the whole blood so that a content of the protease per milliliter of the whole blood is in a range from 1,000 to 10,000,000 U. Further, it is preferable that the FAOD is added to the whole blood so that a content of the FAOD per milliliter of the whole blood is in a range from 500 to 40,000 U.

In the method of the present invention, it is preferable that determining the redox reaction is determining an amount of hydrogen peroxide generated by the redox reaction or an amount of oxygen consumed by the redox reaction. In the method of the present invention, it is preferable that the amount of the hydrogen peroxide is determined using a peroxidase (hereinafter, referred to as "POD") and a substrate that develops color by oxidation.

In the method of the present invention, the substrate that develops color by oxidization is not specifically limited and can be, for example, N-(carboxymethylaminocarbonyl)-4,4'-bis(dimethylamino)diphenylamine sodium, orthophenylenediamine (OPD), and a substrate obtained by combining a Trinder's reagent and 4-aminoantipyrine. Examples of the Trinder's reagent include phenols, phenol derivatives, aniline derivatives, naphthols, naphthol derivatives, naphthylamine, naphthylamine derivatives, and the like. Further, in place of the above-mentioned 4-aminoantipyrine, it is possible to use aminoantipyrine derivatives, vanillin diamine sulfonic acid, methyl benzothiazolinone hydrazone (MBTH), sulfonated methyl benzothiazolinone hydrazone (SMBTH), and the like. Among these chromogenic substrates, N-(carboxymethylaminocarbonyl)-4,4'-bis (dimethylamino)diphenylamine sodium is most preferable.

Next, a method of determining an amount of HbA1c according to the present invention includes: preparing a calibration curve based on a correlation between an amount of glycated hemoglobin determined by the method of determining an amount of glycated hemoglobin according to the present invention and an amount of HbA1c; and substituting the amount of glycated hemoglobin in a whole blood sample determined by the method into the calibration curve to determine an amount of HbA1c in the whole blood sample.

Through a further intensive study, the inventors of the present invention have found that there is a strong correlation between an amount of glycated hemoglobin in a whole blood sample determined according to the method of the present invention and an amount of HbA1c in the whole blood sample. HbA1c is a glycated hemoglobin in which the N-terminal α-amino group in the β-chain of hemoglobin has been glycated. Among various glyeated hemoglobins, HbA1c has served as a particularly important index for the diagnosis etc. of diabetes. According to conventional methods of determining HbA1c, it is necessary that FAOD specifically acts on the glycated N-terminal α-amino group in the β-chain, which is the characteristic structure of HbA1c, among its glycation site and thereafter, the redox reaction caused by the FAOD is determined. In this case, special techniques are required because it is necessary that FAOD to be used has high substrate specificity to the glycated α-amino group and that the FAOD acts on the glycated α-amino group sufficiently, for example. In contrast, according to the method of determining HbA1c of the present invention, HbA1c as an important index for the diagnosis of diabetes can be determined accurately and easily so that the determination of HbA1c can be made practical in clinical tests etc.

In the method of determining HbA1c of the present invention, it is preferable that the calibration curve is prepared based on a correlation between a known amount of HbA1c in a standard sample and an amount of glycated hemoglobin in the standard sample determined by the method of determining an amount of glycated hemoglobin according to the present invention.

Next, a kit used for determining an amount of glycated hemoglobin according to the present invention includes a protease that distinguishes a glycated hemoglobin from other proteins and peptides to degrade the glycated hemoglobin selectively. By using this kit, the method of the present invention can be carried out easily.

In the kit of the present invention, the protease is at least one protease selected from the group consisting of bromelains, papains, trypsins derived from porcine pancreas, metalloproteinases, and proteases derived from Bacillus subtilis. Further, it is preferable that the kit further includes FAOD. Furthermore, it is preferable that a substrate of the FAOD is at least one glycated amine selected from the group consisting of glycated proteins, glycated peptides, and glycated amino acids, and the FAOD acts on at least one of a glycated α-amino group and a glycated side-chain amino group of the glycated amine to catalyze a reaction that causes generation of hydrogen peroxide. Still further, it is preferable that the kit further includes POD and a substrate that develops color by oxidization. The substrate that develops color by oxidization preferably is N-(carboxymethylaminocarbonyl)-4,4'-bis (dimethylamino)diphenylamine sodium.

Next, a reagent used for determining an amount of glycated hemoglobin according to the present invention includes a protease that distinguishes a glycated hemoglobin from other proteins and peptides to degrade the glycated hemoglobin selectively. By using this reagent, the method of the present invention can be carried out easily.

In the reagent of the present invention, the protease is at least one protease selected from the group consisting of bromelains, papains, trypsins derived from porcine pancreas, metalloproteinases, and proteases derived from Bacillus subtilis. Further, it is preferable that the reagent further includes FAOD. Furthermore, it is preferable that a substrate of the FAOD is at least one glycated amine selected from the group consisting of glycated proteins, glycated peptides, and glycated amino acids, and the FAOD acts on at least one of a glycated α-amino group and a glycated side-chain amino group of the glycated amine to catalyze a reaction that causes generation of hydrogen peroxide. Still further, it is preferable that the reagent further includes POD and a substrate that develops color by oxidization. The substrate that develops color by oxidization preferably is N-(carboxymethylaminocarbonyl)-4,4'-bis (dimethylamino)diphenylamine sodium.

BEST MODE FOR CARRYING OUT THE INVENTION

Figure 1:
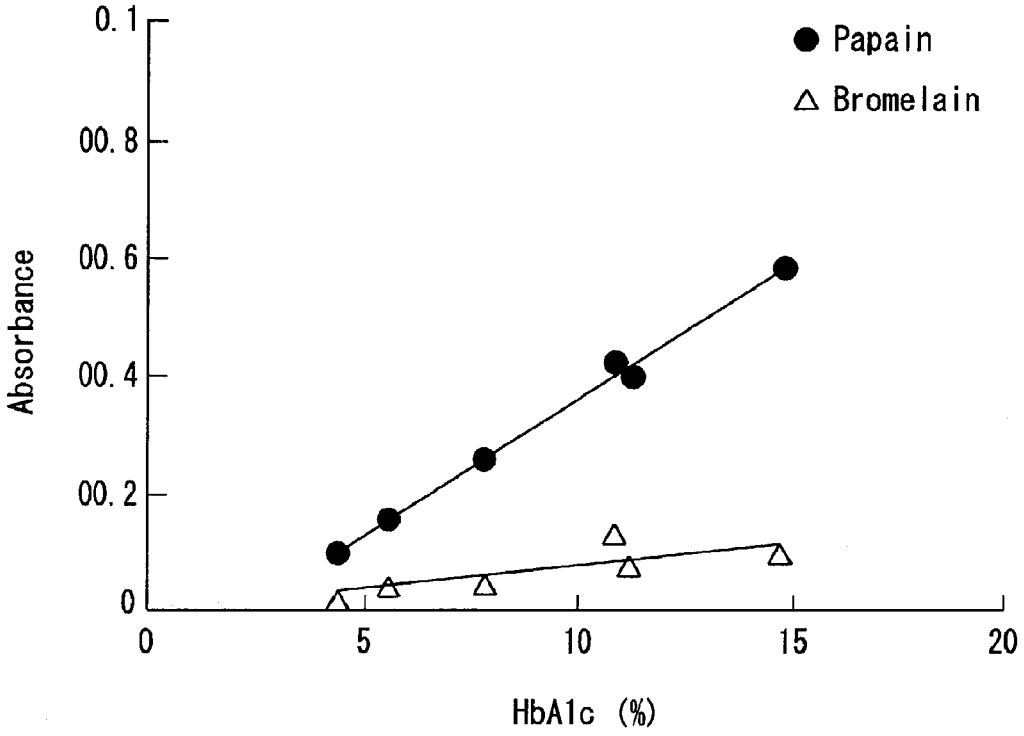
FIG. 1 is a graph showing the correlation between an HbA1c concentration and an absorbance in a method of determining an amount of glycated hemoglobin according to one example of the present invention.

In a method of determining an amount of glycated hemoglobin according to the present invention, FAOD capable of catalyzing a reaction represented by Formula (1) below preferably is used.

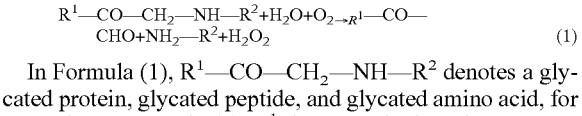

$$R^1—CO—CH_2—NH—R^2+H_2O+O_2 \rightarrow R^1—CO—CHO+NH_2—R^2+H_2O_2 \quad (1)$$

In Formula (1), $R^1—CO—CH_2—NH—R^2$ denotes a glycated protein, glycated peptide, and glycated amino acid, for example. In Formula (1), $R^1$ denotes a hydroxyl group or a residue derided from a sugar that is not yet subjected to the glycation reaction (i.e., sugar moiety). The sugar moiety ($R^1$) is an aldose residue when the unreacted sugar is aldose, and is a ketose residue when the unreacted sugar is ketose. When the unreacted sugar is glucose, for example, the sugar in the glycated product takes on the fructose structure after the glycation reaction due to Amadori rearrangement. In this case, the sugar moiety ($R^1$) is a glucose residue (aldose residue). This sugar moiety ($R^1$) can be represented, for example, by

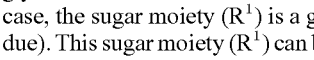

$$—[CH(OH)]_n—CH_2OH$$

where n denotes an integer of 0 to 6.

In Formula (1), $R^2$ is not specifically limited. However, it is to be noted that $R^2$ varies depending on which of an α-amino group and an amino group other than the α-amino group is glycated.

In Formula (1), in the case where an α-amino group is glycated, $R^2$ is an amino acid residue or a peptide residue represented by Formula (2) below.

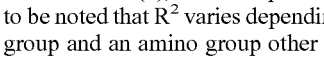

$$—CHR^3—CO—R^4 \quad (2)$$

In Formula (2), $R^3$ denotes an amino-acid side chain group. $R^4$ denotes a hydroxyl group, an amino acid residue, or a peptide residue, and can be represented, for example, by Formula (3) below. In Formula (3), n denotes an integer of 0 or more, and $R^3$ denotes an amino-acid side chain group as described above.

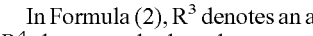

$$—(NH—CR^3H—CO)_n—OH \quad (3)$$

In Formula (1), in the case where an amino group other than the α-amino group is glycated (i.e., an amino-acid side chain group is glycated), $R^2$ is represented by Formula (4) below.

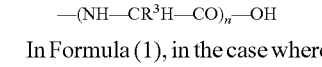

$$—R^5—CH(NH—R^6)—CO—R^7$$

In Formula (4), $R^5$ denotes a portion other than the glycated amino group in the amino-acid side chain group. For example, in the case where the glycated amino acid is lysine, $R^5$ is as follows.

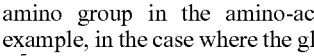

$$—CH_2—CH_2—CH_2—CH_2—$$

On the other hand, in the case where the glycated amino acid is arginine, for example, $R^5$ is as follows.

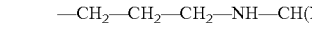

$$—CH_2—CH_2—CH_2—NH—CH(NH_2)—$$

In Formula (4), $R^6$ denotes hydrogen, an amino acid residue, or a peptide residue, and can be represented, for example, by Formula (5) below. In Formula (5), n denotes an integer of 0 or more, and $R^3$ denotes an amino-acid side chain group as described above.

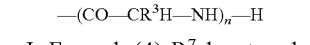

$$—(CO—CR^3H—NH)_n—H \quad (5)$$

In Formula (4), $R^7$ denotes a hydroxyl group, an amino acid residue, or a peptide residue, and can be represented, for example, by Formula (6) below. In Formula (6), n denotes an integer of 0 or more, and $R^3$ denotes an amino-acid side chain group as described above.

$$—(NH—CHR^3—CO)_n—OH \quad (6)$$

A catalytic reaction caused by FAOD to be used in the method of the present invention is not specifically limited as long as it is a reaction represented by Formula (1). However, in Formula (1), it is preferable that the FAOD acts on the glycation site in which a sugar is bound to an amino group other than an α-amino group (i.e., $R^2$ has a structure as represented by Formula (4)). Further, the catalytic function of the FAOD is not limited to such function. In addition to the above catalytic function, the FAOD further may have a catalytic function to act on the glycation site in which a sugar is bound to an α-amino group (i.e., $R^2$ has a structure as represented by Formula (2)).

Examples of such FAOD include those derived from the genus Fusarium, the genus Gibberella, and the genus Aspergillus. More specifically, commercially available FAODs such as Fructosyl Amino Acid Oxidase (trade name, available from Asahi Chemical Industry Co., Ltd.), Ketoamine Oxidase (trade name, available from Genzyme Corporation), and the like can be used, for example.

Hereinafter, an example of a method of determining an amount of glycated hemoglobin according to the present invention will be described.

First, the whole blood is hemolyzed. The method of hemolyzing the whole blood is not specifically limited, and can be, for example, a method using a surfactant, a method using ultrasonic waves, and a method utilizing the difference in osmotic pressure. Among these, the method using a surfactant is preferable on account of the ease of operation.

As the surfactant, nonionic surfactants such as polyoxyethylene-p-t-octylphenyl ether (Triton-type surfactant etc.), polyoxyethylene sorbitan alkyl ester (Tween-type surfactant etc.), polyoxyethylene alkyl ether (Brij-type surfactant etc.), and the like can be used, for example. More specifically, Triton X-100 (trade name), Tween-20 (trade name), Brij 35 (trade name), and the like can be used, for example. Generally, the treatment with the above surfactant can be carried out under the following conditions: in the case where the solution to be treated contains 1 to 10 vol % of blood cells, the surfactant is added to the solution so as to give a concentration of 0.1 to 1 wt % and the resultant mixture is stirred at room temperature for about 5 seconds to 1 minute.

Further, when utilizing the difference in osmotic pressure, to the whole blood was added 2 to 100 times its volume of purified water to cause hemolysis, for example.

Subsequently, the above-mentioned hemolysate sample is treated with the above-mentioned protease, thereby selectively degrading glycated hemoglobin in the sample. Generally, this protease treatment is carried out in a buffer. The treatment conditions are decided as appropriate, for example, depending on the type of the protease to be used, the amount of the glycated hemoglobin, and the like.

In the case where the hemolysate sample is treated using a papain as the protease, the treatment generally is carried out under the following conditions: the protease concentration in the reaction solution in the range from 100 to 30,000 U/L, the hemoglobin concentration in the reaction solution in the range from 0.1 to 40 g/L, the reaction temperature in the range from 15° C. to 60° C., the reaction time in the range from 10 minutes to 40 hours, and the pH in the range from 5 to 9. Further, the type of the buffer is not specifically limited, and can be, for example, Tris-HCl buffer, EPPS buffer, PIPES buffer, phosphate buffer, ADA buffer, citrate buffer, acetate buffer, and the like.

In the case where the hemolysate sample is treated using a metalloproteinase as the protease, the treatment is carried out, for example, under the following conditions: the protease concentration in the reaction solution in the range from 10 to 10,000 KU/L, the hemoglobin concentration in the reaction solution in the range from 0.02 to 40 g/L, the reaction temperature in the range from 15° C. to 60° C., the reaction time in the range from 2 minutes to 40 hours, and the pH in the range from 6 to 11; preferably, the protease concentration in the reaction solution in the range from 100 to 8,000 KU/L, the hemoglobin concentration in the reaction solution in the range from 0.1 to 10 g/L, the reaction temperature in the range from 15° C. to 60° C., the reaction time in the range from 2 minutes to 1 hour, and the pH in the range from 7 to 10. As the buffer, the above-mentioned various buffers also can be used. Further, other proteinases also can be used.

Next, the glycated hemoglobin degradation product obtained through the above-mentioned protease treatment is treated with FAOD. This FAOD treatment catalyzes the reaction represented by Formula (1) above. More specifically, FAOD acts on a glycated amino group in a side chain of a lysine residue and a side chain of an arginine residue in the glycated hemoglobin degradation product, for example. Further, depending on the type of the FAOD to be used, the FAOD further may act on a glycated α-amino group according to its catalytic function.

Similarly to the above-mentioned protease treatment, this FAOD treatment preferably is carried out in a buffer. The buffer is not specifically limited, and the same buffers as used in the protease treatment also can be used in the FAOD treatment.

The FAOD treatment is carried out, for example, under the following conditions: the FAOD concentration in the reaction solution in the range from 200 to 30,000 U/L, the hemoglobin concentration in the reaction solution in the range from 0.02 to 30 g/L, the reaction temperature in the range from 15° C. to 37° C., the reaction time in the range from 1 to 20 minutes, and the pH in the range from 7 to 9; preferably, the FAOD concentration in the range from 1,000 to 20,000 U/L, the hemoglobin concentration in the reaction solution in the range from 0.1 to 5 g/L, the reaction temperature in the range from 15° C. to 37° C., the reaction time in the range from 1 to 5 minutes, and the pH in the range from 7 to 9.

Next, the amount of the hydrogen peroxide generated by the FAOD treatment is determined utilizing a redox reaction, by using the POD and a substrate that develops color by oxidization.

The redox reaction caused by the POD generally is induced in a buffer under the conditions decided as appropriate, for example, depending on the concentration of the hydrogen peroxide and the like. Generally, the redox reaction is induced under the following conditions: the POD concentration in the reaction solution in the range from 1 to 100,000 IU/L, the substrate concentration in the range from 0.0001 to 1 mmol/L, the reaction temperature in the range from 20° C. to 37° C., the reaction time in the range from 1 to 5 minutes, and the pH in the range from 6 to 9; preferably, the POD concentration in the reaction solution in the range from 1,000 to 50,000 IU/L, the substrate concentration in the range from 0.0002 to 0.1 mmol/L, the reaction temperature in the range from 20° C. to 37° C., the reaction time in the range from 1 to 5 minutes, and the pH in the range from 6 to 9. Further, the buffer is not specifically limited, and the same buffers as used in the FAOD treatment also can be used.

It is to be noted here that the amount of the hydrogen peroxide can be determined not only by the above-mentioned enzymic method using the POD etc. but also by an electrical method, for example.

In the case where the substrate that develops color by the above oxidization is used, the concentration of the hydrogen peroxide can be determined by measuring the color development (i.e., the absorbance of the reaction solution) with a spectrophotometer. From the concentration of the hydrogen peroxide, the concentration of the glycated hemoglobin in the sample can be determined.

In the process of determining an amount of glycated hemoglobin as described above, the respective treatment steps may be performed individually as described above, or some of the treatment steps may be performed simultaneously in the following combinations, for example.

1: hemolysis treatment+protease treatment

2: protease treatment+FAOD treatment

3: FAOD treatment+POD treatment

Also, the order in which the FAOD, the POD, and the substrate are added is not specifically limited.

Hereinafter, an example of a method of determining HbA1c according to the present invention will be described.

First, an amount of glycated hemoglobin in a whole blood sample is determined in the above-mentioned manner. On the other hand, a glycated hemoglobin standard solution in which an amount of HbA1c in glycated hemoglobin is known is provided. Then, an amount of glycated hemoglobin in this standard solution is determined in the above-mentioned manner. After that, a calibration curve is prepared that shows the relation between the amount of glycated hemoglobin thus determined and the known amount of HbA1c in this standard solution. Since there is a correlation between the determined amount of glycated hemoglobin and the known amount of HbA1c as described above, an amount of HbA1c in the whole blood sample can be determined by substituting the amount of glycated hemoglobin in the whole blood sample determined by the method of the present invention into this calibration curve. In the preparation of the calibration curve, the determined amount of glycated hemoglobin is not limited to the value finally obtained though the method of the invention, and can be an absorbance of the reaction solution obtained by the POD treatment during the determination process, or an amount of hydrogen peroxide determined based on this absorbance. As described above, according to the method of determining an amount of HbA1c of the present invention, an amount of HbA1c in whole blood can be determined accurately and easily based on an amount of glycated hemoglobin determined by utilizing the correlation discovered by the inventors of the present invention.

EXAMPLES

Example 1

Samples containing glycated hemoglobin and glycated albumin were treated with a papain. Then, a redox reaction thereof was caused by FAOD, and the amount of hydrogen peroxide generated was determined. The samples, reagents, and method used in the determination will be described in the following.

(Samples)

Human serum albumin with glycation ratio of 22.5% (Sigma Chemical Co.)

Human hemoglobin with glycation ratio of 14%

The above human hemoglobin sample was prepared in the following manner, and the glycation ratio thereof was determined by HPLC using an ion exchange column.

(Preparation of Human Hemoglobin)

Whole blood of a healthy subject was centrifuged (1500 G, 10 min) and blood cells were collected. After washing the blood cells with a physiological salt solution several times, a substantially equivalent amount of purified water was added to the blood cells to cause hemolysis. The hemolysate was then centrifuged to remove cell membranes. The solution thus obtained was supplied to GLYCO-GEL II (trade name, available from Pierce Chemical Company). A fraction containing a glycated protein was separated and collected according to the usual method, and the solution thus obtained was used as the human hemoglobin sample.

| (Composition of Redox Solution A) | |
|---|---|
| FAOD (Asahi Chemical Industry Co., Ltd., hereinafter the same) | 2.09 KU/L |
| POD (Type III: Toyobo Co., Ltd., hereinafter the same) | 730 U/L |
| N-(carboxymethylaminocarbonyl)-4,4'-bis(dimethylamino)diphenylamine sodium (Trade name DA 64: Wako Pure Chemical Industries, Ltd., hereinafter the same) | 1.46 mmol/L |
| Tris-HCl buffer (pH 8.0) | 73 mmol/L |

(Method) First, 1 mL of a 1 KU/L papain (available from Sigma Aldrich Co.) was added to 1 mL of the above-mentioned respective samples (human serum albumin, human hemoglobin), and the mixtures were reacted at 40° C. for 24 hours. To 0.018 mL of the thus-obtained solutions was added 0.15 mL of the above redox solution A to cause a redox reaction. Then, 5 minutes after the start of the reaction, the absorbance of these reaction solutions was measured at the main wavelength of 694 nm and the sub-wavelength of 884 nm using a biochemical automatic analysis apparatus (the trade name JCA-BM 8: available from Japan Electron Optics Laboratory Co. Ltd., hereinafter the same). The results are shown in Table 1 below.

Example 2

The above-mentioned respective samples (human serum albumin, human hemoglobin) were treated in the same manner as in Example 1 except that 1 mL of a 1g/L bromelain (available from Amano Enzyme Inc., hereinafter the same) was used in place of the papain, and the absorbance thereof was measured in the same manner as in Example 1. The results are shown in Table 1 below.

Comparative Example 1

The above-mentioned respective samples (human serum albumin, human hemoglobin) were treated in the same manner as in Example 1 except that 1 mL of a 1g/L α-chymotrypsin was used in place of the papain, and the absorbance thereof was measured in the same manner as in Example 1. The results are shown in Table 1 below.

TABLE 1

| | Protease | Human serum albumin (Abs.) | Human hemoglobin (Abs.) |
|---|---|---|---|
| Example 1: | Papain | 0.014 | 0.090 |
| Example 2: | Bromelain | 0.0008 | 0.037 |
| Comparative Example 1: | α-chymotrypsin | 0.063 | 0.042 |

As shown in Table 1, in the case where the papain and bromelain were used as in Examples 1 and 2, the human hemoglobin sample exhibited a high absorbance while the human serum albumin sample exhibited a very low absorbance. These results demonstrate that the papain and bromelain can degrade glycated hemoglobin selectively and hardly degrade glycated albumin. In contrast, in the case where the w-chymotrypsin was used as in Comparative Example 1, both the samples exhibited a high absorbance. These results demonstrate that the w-chymotrypsin acts not only on glycated hemoglobin but also on glycated albumin and thus does not degrade glycated hemoglobin selectively.

Example 3 and Comparative Example 2

Whole blood, plasma, and blood cells were used as samples, and the amount of glycated hemoglobin in the respective samples were determined after treating the respective samples with various proteases.

(Preparation of Whole Blood Samples)

Whole blood was collected from a healthy subject using a blood-collecting vessel containing heparin sodium. The whole blood was diluted 8-fold with purified water to hemolyze the blood cells contained therein. The resultant solution was used as whole blood samples.

(Preparation of Plasma Samples)

Whole blood collected from the above-mentioned healthy subject was centrifuged (1500 G, 10 min) to remove blood cells, and the supernatant obtained was diluted 8-fold with purified water. The resultant solution was used as plasma samples.

(Preparation of Blood Cell Samples)

The blood cells obtained though the above-mentioned centrifugation were diluted 16-fold with purified water to cause hemolysis. The resultant solution was used as blood cell samples.

(Proteases)

A bromelain, papain (available from Hoffmann-La Roche Inc.), elastase (available from Wako Pure Chemical Industries, Ltd.), α-chymotrypsin (available from Wako Pure Chemical Industries, Ltd.), and proteinase K (available from Wako Pure Chemical Industries, Ltd.) were dissolved in purified water, respectively, to prepare 4g/L solutions of the respective proteases.

| (Composition of Redox Solution B) | |
|---|---|
| POD | 20 KU/L |
| DA 64 (trade name) | 0.04 mmol/L |
| Potassium phosphate buffer (pH 7.0) | 0.1 mol/L |
| (Composition of Redox Solution C) | |
| FAOD | 14.3 KU/L |
| Potassium phosphate buffer (pH 7.0) | 0.1 mol/L |

(Determining Method)

First, 0.1 mL of each of the protease solutions and 0.7 mL of potassium phosphate buffer (pH 7.0) were mixed with 0.2 mL of the above-mentioned respective samples, and the resultant mixtures were reacted at 37° C. for 24 hours. Thereafter, the reaction solutions were supplied to Ultra Free 4 Unit 5K (trade name, available from Millipore Corporation) so that the reaction solutions were centrifuged and the supernatants were collected. Subsequently, 45 μL of the redox solution B was added to 25 μl of the respective supernatants, and 20 μl of the redox solution C was further added after 5 minutes to cause a redox reaction. Then, 5 minutes after the start of the reaction, the absorbance of the respective reaction solutions was measured at the main wavelength of 694 nm and the sub-wavelength of 884 nm using the above-mentioned biochemical automatic analysis apparatus. The results are shown in Table 2 below. The bromelain and papain were used in Example 3, and the elastase, α-chymotrypsin, and proteinase K were used in Comparative Example 2.

TABLE 2

| Sample | Protease | Plasma (Abs.) | Blood cells (Abs.) | Whole blood (Abs.) |
|---|---|---|---|---|
| Example 3 | Bromelain | 0.0 | 0.009 | 0.002 |
| | Papain | 0.001 | 0.021 | 0.015 |
| Comparative Example 2 | Elastase | 0.012 | 0.019 | 0.015 |
| | α-chymotrypsin | 0.015 | 0.016 | 0.013 |
| | Proteinase K | 0.036 | 0.027 | 0.034 |

As can be seen from Table 2, in Example 3, substantially no absorption was observed in the plasma samples. These results demonstrate that the proteases used in Example 3 can degrade glycated hemoglobin selectively and hardly degrade glycated albumin etc. derived from plasma, for example. In contrast, in Comparative Example 2, absorption was observed in the plasma samples even though the plasma samples contained no glycated hemoglobin. The reason for this is considered to be that, because the proteases used in Comparative Example 2 degrade glycated proteins without distinguishing glycated hemoglobin from other glycated proteins, glycated albumin and the like also are degraded in the plasma samples, for example, thereby allowing the absorption to be observed in the plasma samples.

Example 4

(Preparation of Glycated hemoglobin Standard Solutions)

HbA1c standard reagents (available from SRL, Inc.) were dissolved in purified water to prepare glycated hemoglobin standard solutions containing HbA1c at concentrations 4.3%, 7.8%, 11.2%, and 14.7%, respectively, while containing 10 g/L hemoglobin. Further, HbA1c standard reagents (available from International Regents Corporation) were dissolved in purified water to prepare glycated hemoglobin standard solutions containing HbA1c at concentrations 5.5% and 10.8%, respectively, while containing 10 g/L hemoglobin.

(Preparation of Various Protease Solutions)

A 2 g/L solution of a bromelain F (available from Amano Enzyme Inc.) and a 1 g/L solution of a papain (available from Hoffmann-La Roche Inc.) were prepared by dissolving the respective proteases in purified water.

(Determining Method)

First, 0.4 mL of each of the protease solutions and 0.1 mL of a 1.0 mol/L potassium phosphate buffer (pH 8.0) were mixed with 0.5 mL of the above-mentioned respective glycated hemoglobin standard solutions with different hemoglobin concentrations. The mixtures were reacted at 37° C. for 24 hours. Thereafter, the reaction solutions were supplied to Ultrafree-MC 5000 MW (trade name, available from Millipore Corporation, hereinafter the same) so that the reaction solutions were centrifuged and the supernatants were collected. Then, 25 μL of the supernatants were diluted 2-fold with purified water. Subsequently, 45 μL of the redox solution B was added to the respective diluted solutions, and 20 μl of the redox solution C was further added after 5 minutes to cause a redox reaction. Then, 5 minutes after the start of the reaction, the absorbance of the respective reaction solutions was measured at the main wavelength of 694 nm and the sub-wavelength of 884 nm using the above-mentioned biochemical automatic analysis apparatus. The results are shown in Table 3 below and in the graph shown in FIG. 1.

TABLE 3

| | HbA1c (%) | | | | | |
|---|---|---|---|---|---|---|
| Protease | 4.3 | 5.5 | 7.8 | 10.8 | 11.2 | 14.7 |
| Papain | 0.010 | 0.016 | 0.026 | 0.043 | 0.041 | 0.059 |
| Bromelain | 0.002 | 0.004 | 0.005 | 0.014 | 0.008 | 0.010 |

FIG. 1 is a graph showing the correlation between an HbA1c concentration and an absorbance in the glycated hemoglobin standard solution. In the case where the papain was used, the correlation equation was $y=210x+2.2$ and the correlation coefficient was $r=0.998$. On the other hand, in the case where the bromelain was used, the correlation equation was $y=1321x+1.0$ and the correlation coefficient was $r=0.968$.

As shown in Table 3 and FIG. 1, the absorbance increases linearly with an increase in the HbA1c concentration in the glycated hemoglobin standard solution. These results demonstrate that there is a strong correlation between an HbA1c concentration and an absorbance (which corresponds to an amount of glycated hemoglobin determined by the method of the present invention). Therefore, by preparing the calibration curve showing the correlation between the HbA1c concentration and the absorbance in advance, it becomes possible to determine an amount of HbA1c in a whole blood sample indirectly using the calibration curve and the amount of glycated hemoglobin in the whole blood sample determined in the above-mentioned manner.

Example 5

Hemolysate samples were treated with a metalloproteinase, a papain, and a protease derived from Bacillus subtilis, and the amounts of glycated hemoglobin in the respective samples were determined according to the method of the present invention. Further, the amounts of HbA1c in the respective samples were determined based on the amounts of glycated hemoglobin thus determined. The samples, reagents, and method used in the determination will be described in the following.

(Preparation of Samples)

Whole blood was collected from healthy subjects and diabetic subjects (12 subjects in total), and allowed to stand for about 6 hours so that red blood cells contained therein were settled. Then, to 0.1 mL of the blood cell fractions were added 1.4 mL of 0.05 wt % Triton X-100 aqueous solutions, respectively, to cause hemolysis. The resultant solutions were used as hemolysate samples.

(Preparation of Standard Solutions)

HbA1c standard reagents (available from International Regents Corporation) were dissolved in 0.05 wt % Triron X-100 aqueous solutions to prepare glycated hemoglobin standard solutions containing HbA1c at concentrations 5.5% and 10.5%, respectively, while containing 200 g/L hemoglobin.

(Preparation of Protease Solutions)

A metalloproteinase (available from Toyobo Co., Ltd.), Protease N "AMANO" (trade name, available from Amano Enzyme Inc.), and a papain (available from Hoffmann-La Roche Inc.) were dissolved in purified water to prepare 1 g/L solutions of the respective proteases.

| (Composition of Redox Solution D) | |
|---|---|
| POD | 20 KU/L |
| DA-64 (trade name) | 0.04 mmol/L |
| Phosphate buffer (pH 8.0) | 0.8 mol/L |
| (Composition of Redox Solution E) | |
| FAOD | 14.3 KU/L |
| Potassium phosphate buffer (pH 8.0) | 0.1 mmol/L |

(Method of Determining Amount of glycated hemoglobin)

First, 0.16 mL of each of the protease solutions and 0.04 mL of a 1.0 mol/L potassium phosphate buffer (pH 8.0) were mixed with 0.2 mL of the above-mentioned respective samples. The mixtures were reacted at 37° C. for 36 hours. Thereafter, the reaction solutions were supplied to the Ultrafree-MC 5000 MW (trade name) so that the reaction solutions were centrifuged and the supernatants were collected. Then, 25 μL of the supernatants were diluted 2-fold with purified water. Subsequently, 45 μL of the redox solution D was added to the respective diluted solutions, and 20 μl of the redox solution E was further added after 5 minutes to cause a redox reaction. Then, 2 minutes after the start of the reaction, the absorbance of the respective reaction solutions was measured at the main wavelength of 751 nm and the sub-wavelength of 884 nm. The absorbance thus measured corresponds to the amount of glycated hemoglobin.

(Method of Determining Hemoglobin Concentration)

Hemoglobin concentrations in the respective samples were determined according to the cyanmethemoglobin method using Hemoglobin Test Wako (trade name, available from Wako Pure Chemical Industries, Ltd.).

(Preparation of Calibration Curve) HbA1c concentrations (%) of the above-mentioned respective standard solutions were measured using an automatic measuring apparatus (the trade name HA-8150: available from ARKRAY, INC.). On the other hand, with regard to the above-mentioned respective standard solutions, the absorbances corresponding to the amounts of glycated hemoglobin were measured by the method of determining an amount of glycated hemoglobin according to the present invention and hemoglobin concentrations were determined by the above-mentioned method of determining a hemoglobin concentration. Then, primary regression equations were prepared for the respective standard solutions based on the percentages (%) obtained by dividing the absorbances corresponding to the amounts of glycated hemoglobin by the hemoglobin concentrations and the measured values (%) given by the automatic measuring apparatus. The primary regression equations thus obtained were used as calibration curves. It is to be noted that the above-mentioned percentages are proportional to the ratios (%) of the glycated hemoglobin. The primary regression equations used as calibration curves in the case where the above-mentioned respective proteases were used are shown in the following.

(Calibration Curve)

| Protease | Primary Regression Equation |
|---|---|
| Metalloproteinase | y = 15846x + 3.2 |
| Protease N "AMANO" | y = 16659x + 3.3 |
| Papain | y = 17258x + 3.4 |

(Method of Determining HbA1c)

Figure 2:
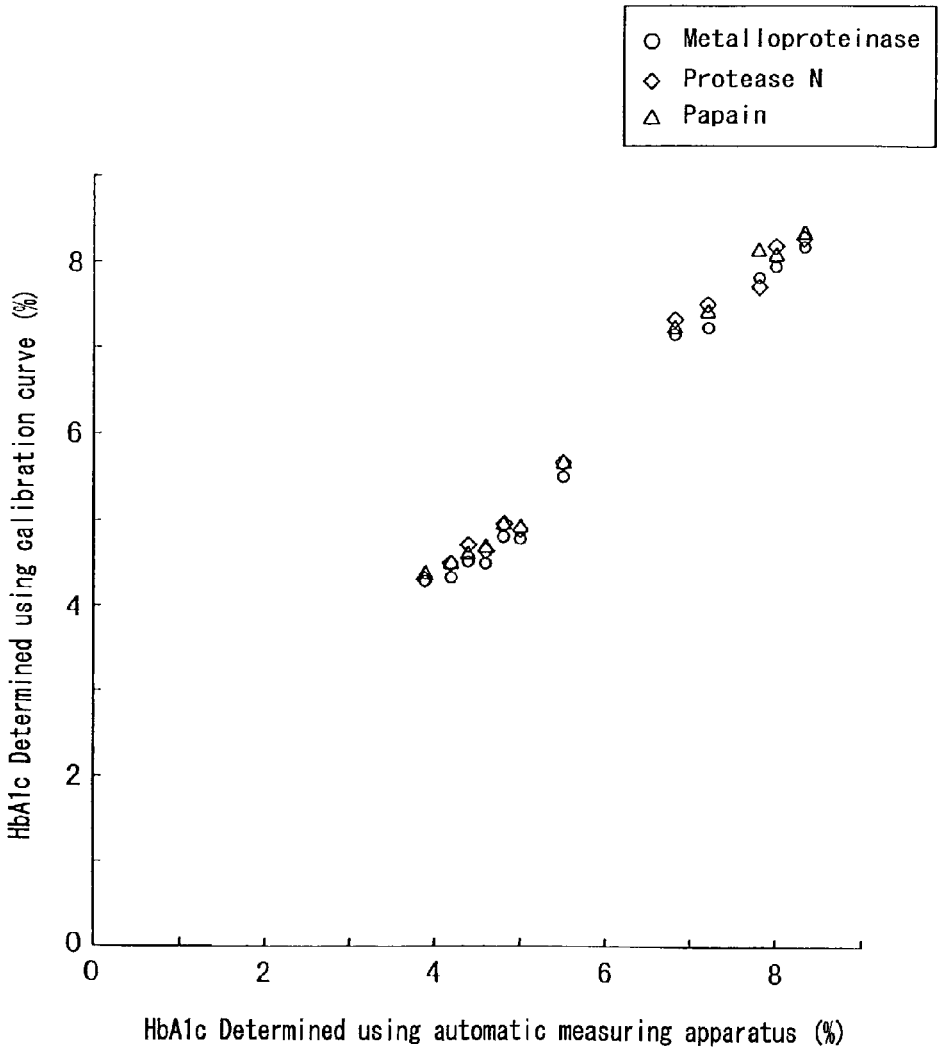
FIG. 2 is a graph showing the correlation between HbA1c (%) determined using a calibration curve and HbA1c (%) measured using an automatic measuring apparatus in a method of determining an amount of glycated hemoglobin according to another example of the present invention.

With regard to the above-mentioned respective hemolysate samples, the absorbances corresponding to the amounts of glycated hemoglobin were measured by the above-mentioned method of determining the amount of glycated hemoglobin, and hemoglobin concentrations were determined by the above-mentioned method of determining a hemoglobin concentration. Then, the percentages obtained by dividing the absorbances corresponding to the amounts of glycated hemoglobin by the hemoglobin concentrations were regarded as the ratios of the glycated hemoglobin, and the amounts of HbA1c in the respective hemolysate samples were determined by substituting the thus-obtained ratios into the above-mentioned respective calibration curves. Further, as controls, the amounts of HbA1c in the respective hemolysate samples were measured using the above-mentioned automatic analysis apparatus. The results are shown in FIG. 2. FIG. 2 is a graph showing the correlations between the amounts of HbA1c determined using the calibration curves according to the method of the present invention and the amounts of HbA1c measured using the automatic measuring apparatus.

As can be seen from FIG. 2, correlation coefficients between HbA1c (%) determined using the calibration curves according to the method of the present invention and HbA1c (%) measured using the automatic measuring apparatus were very high. More specifically, a correlation coefficient in the case where the metalloproteinase was used was 0.9937; a correlation coefficient in the case where the Protease N was used was 0.993; and a correlation coefficient in the case where the papain was used was 0.9941. These results demonstrate that the method of determining an amount of HbA1c according to the present invention can determine the amount of HbA1c with an accuracy comparable to that of the automatic analysis apparatus.

Example 6

Hemolysate samples to which plasma samples have been added were treated with a metalloproteinase. Amounts of glycated hemoglobin in the respective samples were determined to examine the change in the amounts of glycated hemoglobin caused by the addition of the plasma samples.

(Preparation of Samples)

Whole blood collected from a healthy subject (1 subject) and diabetic subjects (diabetic subject 1 and diabetic subject 2) was centrifuged (1000 G, about 15 min), and blood cell fractions and plasma fractions of the respective subjects were collected. Thereafter, predetermined amounts (0 mL, 0.005 mL, 0.010 mL, 0.015 mL, and 0.020 mL) of the plasma fractions of the respective subjects were added to 0.01 mL of the blood cell fractions of the corresponding subjects. Then, to the respective mixtures was added 0.3 mL of the following hemolysis reagent. The resultant solutions were used as hemolysate samples.

Subsequently, 0.065 mL of the following metalloproteinase reagent was added to 0.01 mL of the respective hemolysate samples. The mixtures were incubated at 37° C. for 5 minutes. Then, 0.045 mL of the following redox solution F was further added, and the resultant mixtures were incubated at 37° C. for 2 minutes. Thereafter, the absorbance of the respective reaction solutions was measured at the main wavelength of 751 nm and the sub-wavelength of 805 nm. The absorbance thus measured corresponds to the amount of glycated hemoglobin. Because the amount of the reaction solutions varies depending on the amount of the plasma fractions added thereto, the absorbances shown in Table 4 are the values that have been corrected to show the absorbances per equivalent amounts of the respective reaction solutions.

| (Hemolysis Reagent) | | |
|---|---|---|
| Polyoxyethylene lauryl ether | 9 | g/L |
| CHES buffer (pH 9.4) | 100 | mmol/L |
| (Metalloproteinase Reagent: pH 5.5) | | |
| Metalloproteinase (Toyobo Co., Ltd.) | 4000 | KU/L |
| WST-3 (Dojindo Laboratories) | 2 | mmol/L |
| MES | 5 | mmol/L |
| CaCl2 | 5 | mmol/L |
| NaCl | 50 | mmol/L |

*WST-3: 2-(4-iodophenyl)-3-(2,4-dinitrophenyl)-5-(2,4-disulfophenyl)-2H-tetrazolium monosodium salt

| (Redox Solution F) | | |
|---|---|---|
| FAOD | 30 | KU/L |
| POD | 90 | KU/L |
| DA-64 | 0.06 | mmol/L |
| Phosphate buffer (pH 7.0) | 200 | mmol/L |

TABLE 4

| Added Amount of Plasma fraction (mL) | Healthy subject | Diabetic subject 1 | Diabetic subject 2 |
|---|---|---|---|
| 0 | 0.0215 | 0.0283 | 0.0348 |
| 0.005 | 0.0216 | 0.0278 | 0.343 |
| 0.010 | 0.0196 | 0.0283 | 0.350 |
| 0.015 | 0.0204 | 0.0289 | 0.354 |
| 0.020 | 0.0212 | 0.0288 | 0.359 |

As can be seen from Table 4, even when the plasma fractions were added to the blood cell fractions to give different concentrations, the resultant absorbances differed only slightly. These results demonstrate that, according to the method of the present invention, the amount of glycated hemoglobin can be determined without being affected by the glycated proteins present in plasma.

INDUSTRIAL APPLICABILITY

As specifically described above, according to the method of present invention, a ratio of glycated hemoglobin in a whole blood sample can be determined easily and accurately without separating plasma and blood cells in the whole blood sample. Further, since there is a strong correlation between an amount of glycated hemoglobin determined by the method of the present invention and an amount of HbA1c, by preparing a calibration curve based on this correlation in advance, it becomes possible to determine an amount of HbA1c in a whole blood sample accurately and easily by merely determining the amount of glycated hemoglobin in the whole blood sample. Therefore, by applying the method of the present invention in the field of clinical tests etc., for example, it becomes possible to evaluate a large number of subjects easily, which further increases the reliability and the importance of glycated hemoglobin, especially HbA1c, as an index for the diagnosis and the like of diabetes.

The invention claimed is:

[1. A method of determining an amount of glycated hemoglobin in a sample comprising glycated hemoglobin and glycated albumin from whole blood, comprising:

selectively degrading the glycated hemoglobin in the sample with a protease to give a glycated hemoglobin degradation product;

reacting a glycation site of the glycated hemoglobin degradation product and a fructosyl amino acid oxidoreductase in a redox reaction;

determining a product produced by the redox reaction; and correlating the amount of the product produced with the amount of glycated hemoglobin in the sample.]

[2. The method according to claim 1, wherein the protease is at least one protease selected from the group consisting of bromelains, papains, trypsins derived from porcine pancreas, metalloproteinases, and proteases derived from Bacillus subtilis.]

[3. The method according to claim 1, wherein the glycation site of the glycated hemoglobin degradation product that reacts with the fructosyl amino acid oxidoreductase is a glycated amino group in a side chain of an amino acid residue.]

[4. The method according to claim 3, wherein the glycated amino group in the side chain of the amino acid residue is a glycated amino group in a side chain of at least one of a lysine residue and an arginine residue.]

[5. The method according to claim 1, wherein determining the redox reaction is determining an amount of hydrogen peroxide generated by the redox reaction or an amount of oxygen consumed by the redox reaction.]

[6. The method according to claim 5, wherein the amount of the hydrogen peroxide is determined using a peroxidase and a substrate that develops color by oxidization.]

[7. The method according to claim 6, wherein the substrate that develops color by oxidization is N-(carboxymethylaminocarbonyl)-4,4'-bis(dimethylamino)diphenylamine sodium.]

[8. The method according to claim 1, wherein the protease is added to the whole blood so that a concentration of the protease per milliliter of the whole blood is in a range from 1,000 to 10,000,000 U.]

[9. The method according to claim 1, wherein a substrate of the fructosyl amino acid oxidoreductase is at least one glycated amine selected from the group consisting of glycated proteins, glycated peptides, and glycated amino acids, and the fructosyl amino acid oxidoreductase acts on at least one of a glycated α-amino group and a glycated side-chain amino group of the glycated amine to catalyze a reaction that causes generation of hydrogen peroxide.]

[10. The method according to claim 1, wherein the fructosyl amino acid oxidoreductase is added to the whole blood so that a concentration of the fructosyl amino acid oxidoreductase per milliliter of the whole blood is in a range from 500 to 40,000 U.]

[11. The method according to claim 1, wherein a sample to be used in the method is whole blood that has been subjected to a hemolysis treatment.]

*12. A method of determining an amount of glycated hemoglobin in a sample comprising glycated hemoglobin and glycated albumin from whole blood, comprising:*

*treating the sample with a protease that selectively degrades the glycated hemoglobin over the glycated albumin to give a glycated hemoglobin degradation product, wherein the protease is a metalloproteinase;*

*reacting a glycation site of the glycated hemoglobin degradation product and a fructosyl amino acid oxidoreductase in a redox reaction;*

*determining a product produced by the redox reaction; and*

*correlating the amount of the product produced with the amount of glycated hemoglobin in the sample,*

*wherein the sample to be used in the method is whole blood that has been hemolyzed by a surfactant.*

*13. The method according to claim 12, wherein the glycation site of the glycated hemoglobin degradation product that*

*reacts with the fructosyl amino acid oxidoreductase is a glycated amino group in a side chain of an amino acid residue.*

*14. The method according to claim 13, wherein the glycated amino group in the side chain of the amino acid residue is a glycated amino group in a side chain of at least one of a lysine residue and an arginine residue.*

*15. The method according to claim 12, wherein determining the redox reaction is determining an amount of hydrogen peroxide generated by the redox reaction or an amount of oxygen consumed by the redox reaction.*

*16. The method according to claim 15, wherein the amount of the hydrogen peroxide is determined using a peroxidase and a substrate that develops color by oxidization.*

*17. The method according to claim 16, wherein the substrate that develops color by oxidization is N-(carboxymethylaminocarbonyl)-4,4'-bis(dimethylamino)diphenylamine sodium.*

*18. The method according to claim 12, wherein the protease is added to the whole blood so that a concentration of the protease per milliliter of the whole blood is in a range from 1,000 to 10,000,000 U.*

*19. The method according to claim 12, wherein the glycation site of the glycated hemoglobin degradation product upon which the fructosyl amino acid oxidoreductase acts is at least one glycated amine selected from the group consisting of glycated proteins, glycated peptides, and glycated amino acids, and the fructosyl amino acid oxidoreductase acts on at least one of a glycated α-amino group and a glycated side-chain amino group of the glycated amine to catalyze a reaction that causes generation of hydrogen peroxide.*

*20. The method according to claim 12, wherein the fructosyl amino acid oxidoreductase is added to the whole blood so that a concentration of the fructosyl amino acid oxidoreductase per milliliter of the whole blood is in a range from 500 to 40,000 U.*

*21. The method according to claim 12, wherein the fructosyl amino acid oxidoreductase is selected from the group consisting of Fusarium, Gibberella and Aspergillus.*

*22. The method according to claim 12, wherein the treatment of the sample with the protease is carried out in a buffer.*

*23. The method according to claim 22, where the buffer is selected from the group consisting of Tris-HCl buffer, EPPS buffer, PIPES buffer, phosphate buffer, ADA buffer, citrate buffer and acetate buffer.*

*24. The method according to claim 12, wherein the treatment of the sample with the protease is carried out at a pH in a range from 6 to 11.*

*25. The method according to claim 12, wherein the whole blood sample to be used in the method has been centrifuged.*

*26. The method according to claim 12, wherein the surfactant is nonionic.*

*27. The method according to claim 26, wherein the nonionic surfactant is selected from the group consisting of polyoxyethylene-p-t-octylphenyl ether, polyoxyethylene sorbitan alkyl ester and polyoxyethylene alkyl ether.*

* * * * *